United States Patent [19]

Slocum

[11] Patent Number: 4,612,918
[45] Date of Patent: Sep. 23, 1986

[54] METHOD OF ELIMINATING CANINE CAUDA EQUINA SYNDROME

[76] Inventor: Barclay Slocum, 241 Spy Glass Dr., Eugene, Oreg. 97401

[21] Appl. No.: 661,351

[22] Filed: Oct. 16, 1984

[51] Int. Cl.$^4$ .............................................. A61F 5/00
[52] U.S. Cl. .................................... 128/69; 128/92 B
[58] Field of Search ...................... 128/69, 92 B, 92 R, 128/92 A

[56] References Cited

U.S. PATENT DOCUMENTS

| | | | |
|---|---|---|---|
| 2,677,369 | 5/1954 | Knowles | 128/69 |
| 3,623,164 | 11/1971 | Bokros | 128/92 B |
| 3,997,138 | 12/1976 | Crock | 128/92 B |
| 4,289,123 | 9/1981 | Dunn | 128/92 B |
| 4,401,112 | 8/1983 | Rezaian | 128/92 B |

FOREIGN PATENT DOCUMENTS

| | | | |
|---|---|---|---|
| 2387637 | 12/1978 | France | 128/92 B |
| 644472 | 1/1979 | U.S.S.R. | 128/69 |

OTHER PUBLICATIONS

B. Slocum, DVM, T. Devine, MS, L7-S1 Fixation-Fusion for Treatment of Cauda Equina Compression in the Dog, Journal of The American Veterinary Medical Association, vol. 188, No. 1, Jan. 1, 1986.

Lenehan, T. M., Canine Cauda Equina Syndrome, Compend. Cont. Educ. Pract. Vet., 1983; 5:941-951.
Tarvin, G., Prata, R. G., Lumbosacral Stenosis in Dogs, J. Am. Vet. Med. Assoc., 1980; 177:154-159.
Berzon, J. L., Dueland, R., Cauda Equina Syndrome: Pathophysiology and Report of Seven Cases, J. Am. Anim. Hosp. Assoc., 1970; 15:635-643.
Oliver, J. E., Selcer, R. R., Simpson S., Cauda Equina Compression from Lumbosacral Malarticulation and Malformation in the Dog, J. Am. Vet. Med. Assoc., 1978; 173:207-214.
Orthopedic Diseases of the Spine, pp. 751-753.

Primary Examiner—Clifford D. Crowder
Attorney, Agent, or Firm—Kolisch, Hartwell & Dickinson

[57] ABSTRACT

A method of eliminating canine cauda equina syndrome is disclosed. The method includes the steps of dorsally separating the sacrum from $L_7$, substantially aligning the caudal articular processes on $L_7$ with their respective articular facets on $S_1$ thereby relieving pressure on the nerves passing through the $L_7 S_1$ juncture. $L_7$ is fixed relative $S_1$ by fusing $L_7$ to $S_1$ by grafting bones, by anchoring $L_7$ relative $S_1$ by inserting a pin through the two vertebrae, or by providing a rearward limit of movement for $L_7$. The methods of fixing may be used individually or in combination to eliminate the syndrome.

5 Claims, 8 Drawing Figures

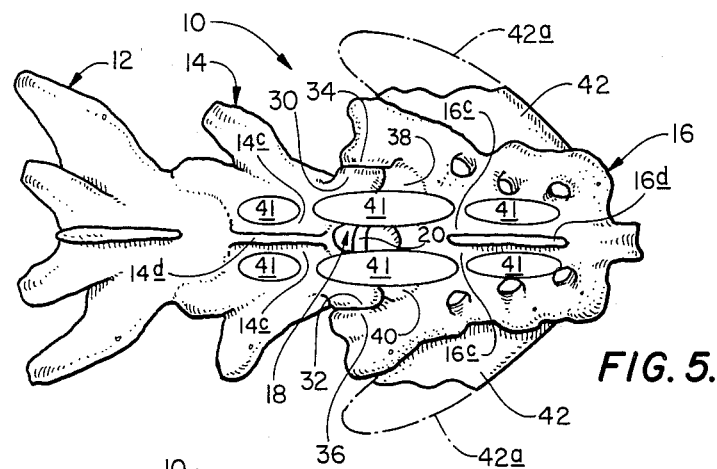

METHOD OF ELIMINATING CANINE CAUDA EQUINA SYNDROME

BACKGROUND AND SUMMARY OF THE INVENTION

The instant invention relates to a method of eliminating canine cauda equina syndrome. Specifically, the method disclosed substantially reduces or eliminates pinching of nerves between the last (seventh) lumbar vertebrae ($L_7$) and the first sacral vertebrae ($S_1$).

Cauda equina syndrome occurs when the sacral and caudal nerves, the cauda equina, passing through the juncture of the seventh lumbar vertebrae ($L_7$) and the first sacral vertebrae ($S_1$) are compressed as a result of a degenerative disc between $L_7$ and $S_1$. Additionally, the peripheral nerves exiting the spine between $L_7$ and $S_1$ may be compressed. The fibrous components of the $L_7S_1$ disc and the ligamentum flavum, which covers the dorsal juncture between the vertebrae, protrude into the cavity through which the nerves pass. In minor cases, the animal will exhibit discomfort when it tenses or when it attempts to move its hind body portion. In more severe cases, the animal will suffer extreme discomfort and will probably elect to remain immobile as much as possible. Because the nerves affected control voluntary and involuntary body functions, the animal may eventually lose control of urinary and rectal functions as well as reproductive ability.

Known procedures for minimizing or eliminating cauda equina syndrome include a laminectomy for removing a portion of either or both $L_7$ and $S_1$ vertebrae. This accomplishes the desired decompression of the nerves passing therethrough, but results in an unstable spinal column and ultimately in a useless animal.

Another known method involves fusing the vertebrae about the $L_7S_1$ juncture from the ventral side of the spinal column. Bone spurs will generally be present, thereby increasing the difficulty of the operation. Yet another known method of reducing cauda equina syndrome is to remove the ligamentum flavum from the dorsal portion of the $L_7S_1$ juncture. Finally, a discectomy of the dorsal annulus fibrosis may reduce the animal's pain.

All of the known methods will provide some degree of relief for the animal, but are not successful in the long run. These known procedures leave portions of the intervertebral disc or ligamentum flavum which may ultimately compress the nerves passing through the $L_7S_1$ juncture or leave the spine unstable.

It is therefore an object of the instant invention to provide a method of eliminating canine cauda equina syndrome, which is a one-time procedure and provides continuous relief from nerve compression produced by the breakdown of the intervertebral disc and collapse of the $L_7S_1$ intervertebral disc space.

Another object of the instant invention is to provide a method of eliminating canine cauda equina syndrome by fixing $L_7$ relative $S_1$ in a position whereby compression is not applied on the nerves passing through the $L_7S_1$ juncture.

The instant invention teaches a method of eliminating canine cauda equina syndrome by dorsally separating $S_1$ and its associated sacral vertebrae from $L_7$, thereby relieving pressure on the nerves passing through the $L_7S_1$ juncture. $L_7$ is fixed relative $S_1$ with the caudal articular processes on $L_7$ substantially aligning with their respective articular facets on $S_1$. $L_7$ may be fixed relative $S_1$ by fusing $L_7$ to $S_1$, by anchoring $L_7$ relative $S_1$ by inserting a pin through the articular facet on each caudal articular process on $L_7$ and through the respective articular facet on $S_1$, or by a combination of fusing and inserting a pin in both vertebrae.

Other objects and advantages of the instant invention will become more fully apparent as the description which follows is read in conjunction with the drawings.

DESCRIPTION OF THE DRAWINGS

FIG. 5 is a view similar to FIG. 3 depicting a fusing procedure.

FIG. 6 is a dorsal view similar to FIG. 3, showing placement of anchoring pins.

FIG. 7 is a view similar to FIG. 5 depicting anchor pins in place.

FIG. 8 is a view similar to FIG. 3 depicting an alternate method of preventing rearward movement of $L_7$.

DETAILED DESCRIPTION OF THE INVENTION

Figure 1:
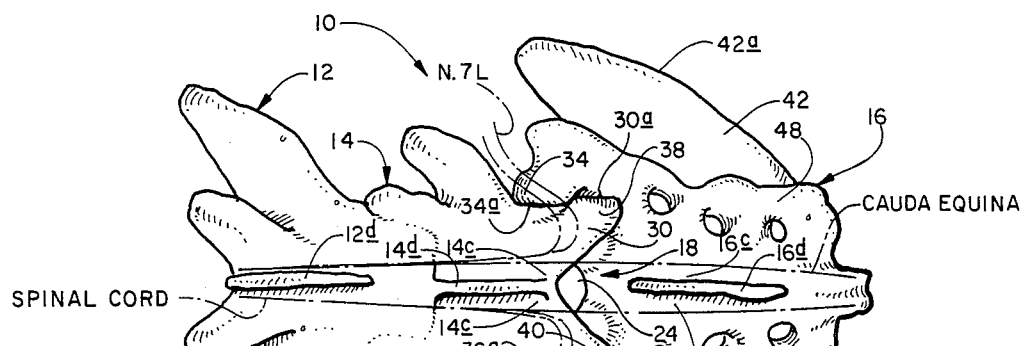
FIG. 1 is a dorsal view of a collapsed $L_7S_1$ juncture, with the spinal canal and nerves shown in phantom lines.
Figure 2:
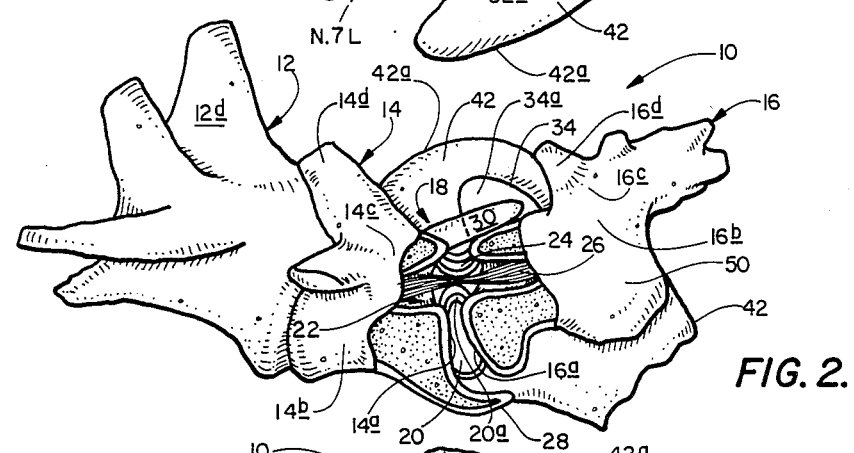
FIG. 2 is a side view of the juncture shown in FIG. 1 with portions broken away to show detail.

Returning now to the drawings, and initially to FIGS. 1 and 2, a portion of a canine spinal column of the lumbar-sacral region is shown generally at 10. Specifically, the sixth lumbar vertebrae ($L_6$), is shown at 12, the seventh lumbar vertebrae ($L_7$), is shown at 14 and the sacrum, comprising fused sacral vertebrae $S_1$, $S_2$ and $S_3$ is shown generally at 16. The region shown at 18 is what is referred to herein as the $L_7S_1$ juncture.

Referring now to FIG. 2, an intervertebral disc 20 is located between $L_7$ and $S_1$. $L_7$ and $S_1$ have vertebral body end plates 14a, 16a, respectively. The disc is shown in a collapsed condition between these plates. The dorsal annulus fibrosis, 20a, of disc 20 protrudes into a canal 22 passing through $L_7$ and $S_1$.

Ligamentum flavum 24 spans the void on the dorsal side of the spinal canal between $L_7$ and $S_1$. It also protrudes downward into canal 22. The cauda equina 26 is shown passing through canal 22 in a compressed condition, under the influence of the protrusion of the annulus fibrosis 20a and ligamentum flavum 24.

A bone spur 28, in the form of a pathologic spondylitic bridge, has formed as the result of irritation produced by collapsed disc 20.

Returning now to FIG. 1, $L_7$ has two caudal articular processes 30, 32 extending laterally and rearwardly of the vertebrate body 14b. Each caudal articular processes has an articular facet as shown at 30a and 32a. $S_1$ has a pair of cranial articular processes, 34, 36, which also have articular facets 34a, 36a, respectively, thereon which, in normal conditions, receive and articulate with the articular facets on the caudal articular processes of $L_7$. As shown in FIG. 1, the caudal articular processes have slipped rearward relative the sacrum and are resting in the sacral recesses 38, 40 of the sacrum.

Figure 3:
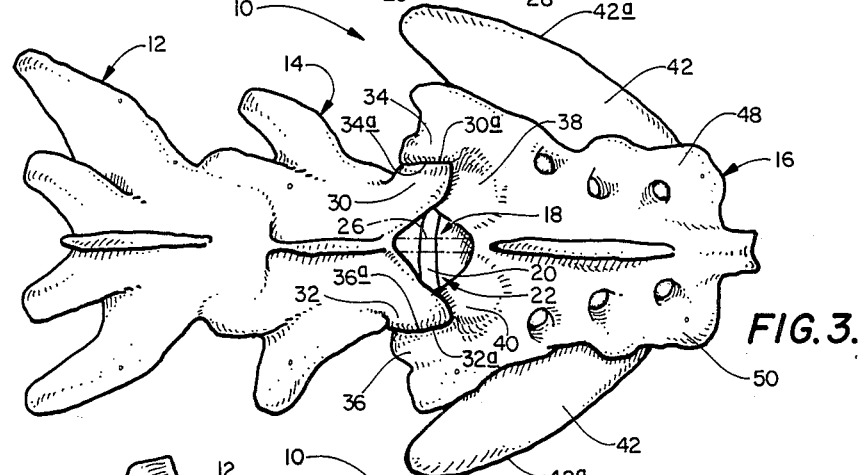
FIG. 3 is a dorsal view of an $L_7S_1$ juncture with the lumbar vertebrae separated from the sacrum.
Figure 4:
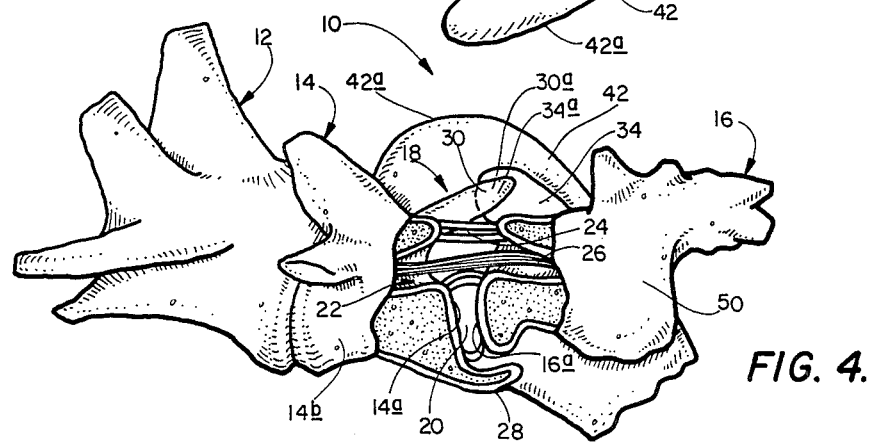
FIG. 4 is a side view of FIG. 3 with portions broken away to show detail.

The method of the invention includes dorsally separating the sacrum from $L_7$. This is accomplished through routine surgical technique once the spinal canal in the $L_7S_1$ region has been dorsally exposed. The articular facets on the $L_7$ caudal articular processes are substantially aligned (FIG. 3) with the respective articular facets on $S_1$ and are fixed in their proper position. The separating and fixing thus described cause disc 20 and ligamentum flavum 24 to be stretched, as shown in FIG. 4, thereby to decompress the nerves running through the canal and the peripheral nerves which exit between $L_7$ and $S_1$.

If it appears that the ligamentum flavum has lost resiliency and will not stretch out, thereby clearing the channel, the ligamentum flavum may be surgically removed to clear the channel.

Referring now to FIG. 5, one technique for fixing $L_7$ relative $S_1$ is to fuse $L_7$ to $S_1$. This may be accomplished through the technique of cortical and/or cancellous bone grating along the lamina, 14c, 16c, between the dorsal spinus processes 14d, 16d, of the seventh lumbar and sacral vertebrae, respectively, such as depicted at 41. A fused spinal column in the region of $L_7S_1$ will be formed. Generally, when such fusion has been accomplished, spondylitic bridge 28 will fuse with $S_1$, thereby completing fusion of $L_7S_1$. In this respect, the procedure thus far described compliments natural healing processes already under way.

When fusion is accomplished through the bone grafting technique, a ready source of bone is the ilium 42. Specifically, the dorsal portion of the wing 42a of the ilium may be removed down to the level of the sacrum to provide material for bone graft, although any bone material may be used. Musculature overlying the spine will hold the bone grafting material in place during the healing process, typically, 2 to 4 months.

In situations where the degeneration of disc 20 has progressed to a point where it is virtually eliminated through pressure between the vertebral body end plates of $L_7$ and $S_1$, it is necessary to provide complete immobilization of the $L_7S_1$ juncture. This may be accomplished by inserting stainless steel pins 44, 46 through the $L_7$ caudal articular processes, as shown. The pins extend through the articular facets of the $S_1$ cranial articular processes, thereby unifying $S_1$ to $L_7$.

If there has been degeneration of the sacrum, the pins may be extended into the pelvis by drilling through the sacroiliac articulation 48, 50 of $S_1$ and extending the pin into the ilium. Such a procedure results in the placement of pin 46 in FIG. 6.

In an extreme case of disc degeneration, or in the case of a very large animal, it may be desirable to fix $L_7$ relative $S_1$ by both fusing $L_7$ to $S_1$ by means of bone grafting and additionally by anchoring $L_7$ relative $S_1$ through the use of stainless steel pins. The result of this procedure is depicted in FIG. 7.

In mild cases, the syndrome may be eliminated by fixing $L_7$ relative $S_1$ by means of inserting screws 52, 54 just caudal to cranial articular processes 34 and 36 to prevent rearward movement of $L_7$ relative $S_1$, as shown in FIG. 8.

The procedure is particularly useful in medium to large animals, such as Labradors, Chesapeakes, Golden Retrievers, etc. The symptoms are well known in that the animal appears to be sore, is less active or may be considered to be lazy. Most observers would conclude that the animal is just getting old, although the onset of cauda equina syndrome may occur as early as three to five years of age. Typically, the syndrome will occur when the animal is eight to ten years of age, and when a healthy animal would still be expected to have four to five good years left in its life.

Although a preferred method of performing the procedure is disclosed, it should be appreciated that variations and modifications may be made to the method without departing from the spirit of the invention.

It is claimed and desired to secure by Letters Patent:

1. The method of eliminating canine cauda equina syndrome comprising:
   dorsally separating the sacrum from $L_7$,
   substantially aligning the caudal articular processes on $L_7$ with their respective articular facets on $S_1$,
   by said aligning, relieving pressure on the nerves passing through the $L_7S_1$ junction,
   fixing $L_7$ relative $S_1$ with the caudal articular processes on $L_7$ substantially aligned with their respective articular facets on $S_1$ by inserting a pin through the articular facet on each caudal articular process on $L_7$ and through the respective articular facet on $S_1$, and
   fusing $L_7$ to $S_1$ by laying bone grafts along the dorsal spinus processes and lamina of $L_7$ and $S_1$.

2. The method of claim 1, wherein the pins are inserted through each articular facet on $S_1$ and extended laterally through $S_1$ to the pelvis.

3. The method of claim 1, which further includes removing the ligamentum flavum between $L_7$ and $S_1$.

4. A method of eliminating canine cauda equina syndrome comprising:
   dorsally separating the sacrum from $L_7$,
   substantially aligning the caudal articular processes on $L_7$ with their respective articular facets on $S_1$,
   by said aligning, relieving pressure on the nerves passing through the $L_7S_1$ junction,
   anchoring $L_7$ relative $S_1$ by inserting a pin through the articular facet on each caudal articular process on $L_7$ and through the respective articular facet on $S_1$ with the caudal articular processes on $L_7$ substantially aligned with their respective articular facets on $S_1$,
   extending the pin laterally through $S_1$ to the pelvis, and
   laying bone grafts along the dorsal spinus processes and lamina of $L_7$ and $S_1$ thereby to fuse $L_7$ and $S_1$.

5. A method of eliminating canine cauda equina syndrome comprising:
   dorsally separating the sacrum from $L_7$,
   substantially aligning the caudal articular processes on $L_7$ with the respective articular facets on $S_1$,
   by said aligning, relieving pressure on the nerves passing through the $L_7S_1$ juncture, and
   inserting screws into the cranial articular processes of $S_1$ in a position setting a rearward limit of travel for $L_7$ to prevent rearward movement of the caudal articular processes on $L_7$, thereby fixing $L_7$ relative $S_1$.

* * * * *